US00PP35777P2

(12) United States Plant Patent
Olesen

(10) Patent No.: US PP35,777 P2
(45) Date of Patent: Apr. 30, 2024

(54) MINIATURE ROSE PLANT NAMED 'POULPAH119'

(50) Latin Name: *Rosa hybrida*
Varietal Denomination: Poulpah119

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 18/445,491

(22) Filed: Sep. 8, 2023

(30) Foreign Application Priority Data

Sep. 30, 2022 (QZ) ..... PBR 2022/2166

(51) Int. Cl.
*A01H 5/02* (2018.01)
*A01H 6/74* (2018.01)

(52) U.S. Cl.
USPC ..... Plt./124

(58) Field of Classification Search
USPC ..... Plt./125, 124, 118, 117, 145, 144, 103
CPC . A01H 5/02; A01H 5/00; A01H 6/749; A01H 6/74
See application file for complete search history.

(56) References Cited

U.S. PATENT DOCUMENTS

PP33,199 P2 * 6/2021 Olesen ..... Plt./124

OTHER PUBLICATIONS

CPVO Register Version 4.12.14, retrieved on Nov. 22, 2023 at https://online.plantvarieties.eu/publicConsultationDetails?registerId=20222166&denomination=poulpah119, 2 pp. (Year: 2023).*

* cited by examiner

*Primary Examiner* — June Hwu

(57) ABSTRACT

A new garden rose plant of the miniature class which has abundant, white flowers and attractive foliage. This new and distinct variety has shown to be uniform and stable in the resulting generations from asexual propagation.

2 Drawing Sheets

Botanical designation: *Rosa hybrida.*
Variety denomination 'Poulpah119'.
This application claims priority to Plant Breeder's Rights Application Number 2022/2166, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpah119', originated as a single seedling from the stated cross.

The new variety may be distinguished from its male pollen parent and female seed parent primarily by the following characteristics. The female seed parent has flowers with a general tonality of light yellow, while 'Poulpah119' is white or near white. While the claimed plant has white flowers with over 100 petals, the male pollen parent has white flowers with about 45 petals.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance.

This combination of qualities is not present in previously available commercial cultivars of this type, known to the inventor, and distinguish 'Poulpah119' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpah119' was selected in the spring of 2016 by the inventor as a single plant from the progeny of the aforementioned hybridization.

Asexual reproduction of 'Poulpah119' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpah119' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah119'.

Specifically illustrated in FIG. 1 of the drawings are open flowers viewed from above and the side, sepals detached revealing reproductive flower parts, flower buds at various stages of development, and detached flower petals.

Figure 1:
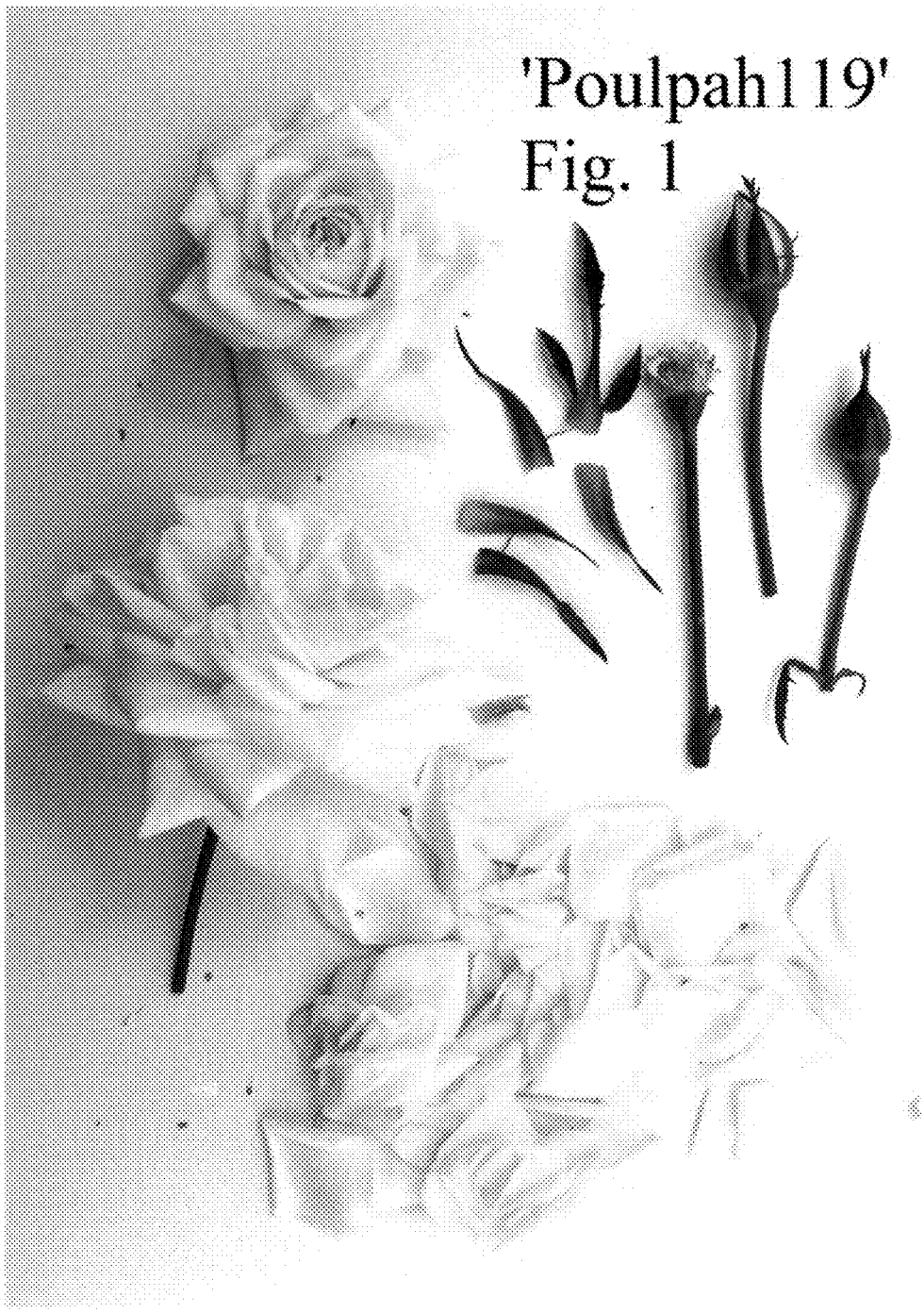
Figure 2:
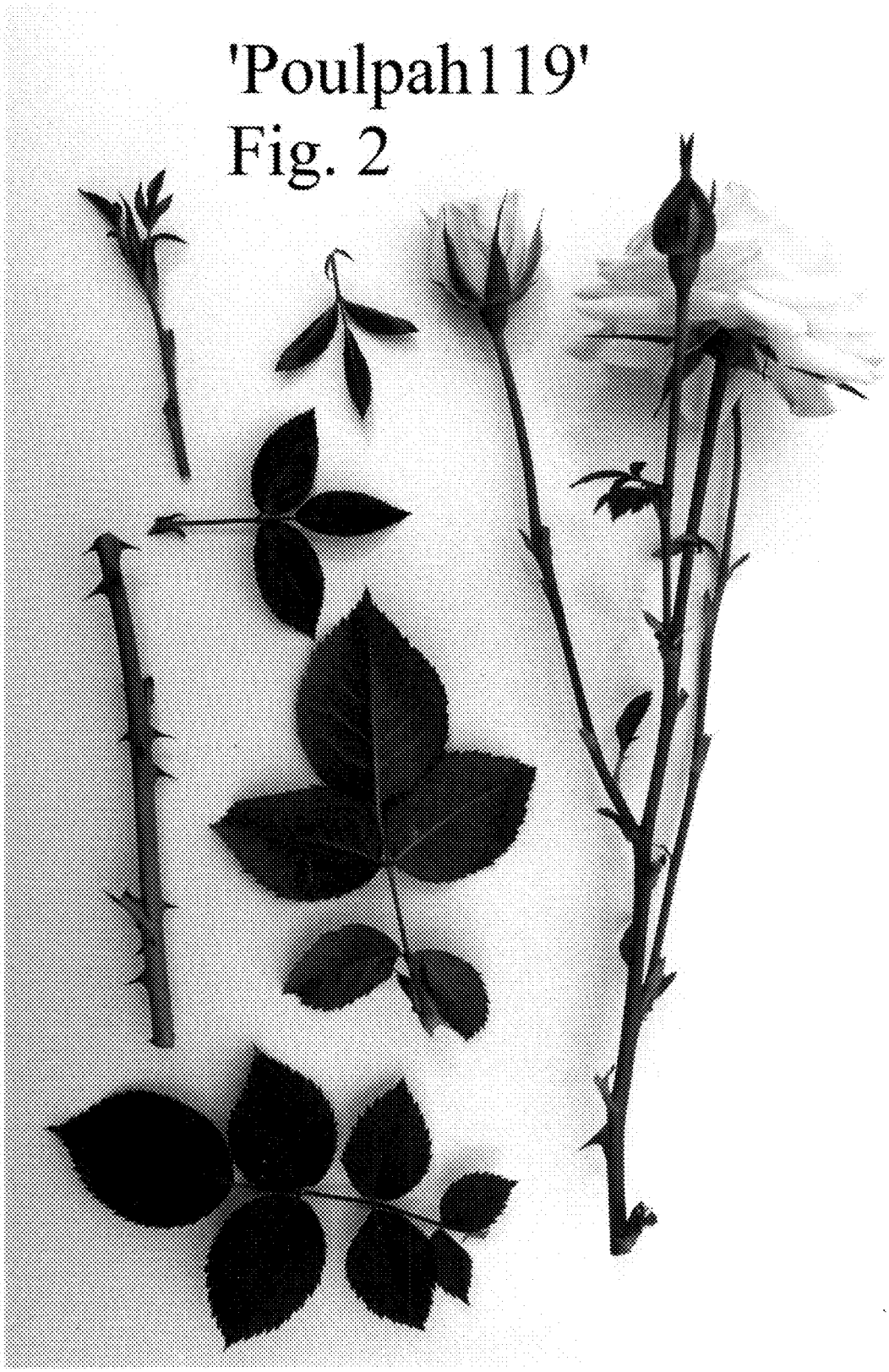

Specifically illustrated in FIG. 2 of the drawings are a cluster of flowers on a branch, bare stem exhibiting prickles, mature leaves, and juvenile leaves exhibiting anthocyanin. Plants shown are 5 months of age.

DETAILED DESCRIPTION OF THE VARIETY

The following is a description of 'Poulpah119', as observed in its growth in an indoor glasshouse nursery in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah104', U.S. Plant Pat. No. 33,199 are compared to the claimed plant. While 'Poulpah119' has 112 flower petals, 'Poulpah104' has 75 to 80 flower petals. The claimed plant has a flower diameter of 90 mm while 'Poulpah104' has a flower diameter of 60 mm. Upon opening, the inner petals on flowers of 'Poulpah119' are Yellow Group 11C in color while the inner petals of 'Poulpah104' are White Group 155B.

FLOWER AND FLOWER BUD

Blooming habit: Continuous.

Flower bud:

- *Size*.—Upon opening, 24 mm in length from base of receptacle to end of bud. Bud diameter is 14 mm.
- *Bud form*.—Urceolate.
- *Bud color*.—As sepals divide petals are Yellow-White Group 158A.
- *Sepal inner surface*.—Color: Green Group 138C. Surface: Lightly pubescent.
- *Sepal outer surface*.—Color: Yellow-Green Group 147A with intonations' of Greyed-Purple Group 187A. Texture: Smooth.
- *Sepal shape*.—Apex: Cirrhose. Base: Flat at union with receptacle.
- *Sepal margin*.—Margins have strong foliaceous appendages on three of the five sepals.
- *Sepal size*.—About 45 to 55 mm long, 8 mm wide.
- *Receptacle*.—Texture: Smooth. Size: 9 mm in height, 8 mm wide. Color: Yellow-Green Group 144A. Shape: Campanulate.
- *Pedicel*.—Surface: Smooth. Length: About 60 to 70 mm. Diameter: 3.5 mm on average. Color: Yellow-Green Group 144A. Strength: Strong.
- *Peduncle*.—Length: 2 to 3 cm. Diameter: About 4 mm. Color: Yellow-Green Group 144A. Texture: Smooth.

Flower bud development: Flower buds are borne single in clusters of flower buds per stem.

Flower bloom:

- *Fragrance*.—Light to Moderate.
- *Duration*.—The blooms have a duration on the plant of approximately 21 days. Petals fall cleanly away from plant after flowers have fully matured.
- *Size*.—Flower diameter is about 90 mm when fully open. Flower depth is 45 mm.
- *Flower shape*.—High centered, very double, with a high pointed center which is tightly closed.
- *Shape of flower, side view*.—The upper portion is flat convex. The lower portion is concave.

Petalage: Under normal conditions, flowers have about 112 petals.

General tonality of flower: Open flowers are White Group 155B.

Petal color:

- *Upon opening, outer petals*.—Upper surface: Yellow Group 11D. Lower surface: White Group 155B with intonations of Yellow-White Group 158B at the basal zone.
- *Upon opening, inner petals*.—Upper surface: Yellow Group 11C. Lower surface: Yellow Group 11C.
- *After opening, outer petals*.—Upper surface: White Group 155B. No distinctive coloration at the petal base. Lower surface: White Group 155B with intonations of Yellow Group 11D at basal zone.
- *After opening, inner petals*.—Upper surface: White Group 155B. No distinctive coloration at the petal base. Lower surface: White Group 155B with intonations of Yellow Group 11D at basal zone.

Petals:

- *Petal reflex*.—Bilateral reflexed strong.
- *Margin*.—Entire and uniform. Moderate undulations.
- *Shape*.—Broad and elliptic. Apex shape: Rounded. Base shape: Acute.
- *Size*.—48 mm (l)×40 mm (w).
- *Texture*.—Smooth.
- *Thickness*.—Average.

Petaloids:

- *Size*.—12 mm (l) by 6 mm (w).
- *Quantity*.—About 30.
- *Shape*.—Elliptical with an acute base and rounded apices.
- *Color*.—White Group 155B with intonations of Yellow Group 11D at basal zone on both the upper and lower petaloid surface.

Reproductive flower parts:

- *Pollen*.—None observed.
- *Anthers*.—Size: 2 mm in length. Color: Greyed-Orange Group 164A. Quantity: 27 on average.
- *Filaments*.—Color: Green-Yellow Group 1C. Length: About 4 mm.
- *Pistils*.—Length: 11 mm. Quantity: 25 on average.
- *Stigmas*.—Color: White Group 155C.
- *Styles*.—Color: White Group 155C.
- *Location of stigmas*.—Superior in location relative to the length of the filaments and the height of the anthers.
- *Hips*.—None Observed.

PLANT

Plant growth: Upright. Plants are 50 to 55 cm in height, and 38 cm wide.

Stems:

- *Color of juvenile growth*.—Yellow-Green Group 144A.
- *Color of mature growth*.—Yellow-Green Group 144A.
- *Length*.—Canes are about 35 cm from the base of the plant to the flowering portion.
- *Diameter*.—About 6 mm.
- *Internodes*.—On mature canes about 50 mm between nodes.
- *Surface texture*.—Young wood: Smooth. Older wood: Smooth.

Long prickles:

*Incidence.*—7 prickles per 10 cm of stem.

*Size.*—Average length of prickles on mature stems is 9 mm.

*Shape.*—Upper portion is linear. Lower portion is concave.

*Color.*—Juvenile prickles: Yellow-Green Group 146C. Mature prickles: Greyed-Orange Group 164A.

Plant foliage:

*Compound leaf.*—133 mm (l)×85 (w).

*Quantity.*—2 leaves per 10 cm of stem on average.

*Leaf bearing angle to the stem.*—45 degrees.

*Color of juvenile foliage.*—Upper and lower surface: Yellow-Green Group 146B with strong intonations of Greyed-Purple Group 183B.

*Color of mature foliage.*—Upper side: Yellow-Green Group 147A. Lower side: Yellow-Green Group 147B.

Plant leaves and leaflets:

*Stipules.*—Size: 9 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 20 mm. Diameter: 2 mm. Upper surface color: Yellow-Green Group 144A. Lower surface color: Yellow-Green Group 144A.

*Rachis.*—Length: 60 mm Upper surface color: Yellow-Green Group 144A. Lower surface color: Yellow-Green Group 144A.

*Leaflet.*—Quantity: Normally 5 to 7 leaflets. Margins: Serrated. Size: Terminal leaflets are about 60 mm long, 38 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold Hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah119' substantially as described and illustrated herein.

* * * * *

'Poulpah119'

'Poulpah119'